US011389200B1

(12) United States Patent
Blackwell et al.

(10) Patent No.: US 11,389,200 B1
(45) Date of Patent: Jul. 19, 2022

(54) SYSTEMS AND METHODS FOR LEG STABILIZATION DURING KNEE ARTHROPLASTY SURGERY

(71) Applicant: GLOBUS MEDICAL, INC., Audubon, PA (US)

(72) Inventors: Timothy Blackwell, Phoenixville, PA (US); Hayden Cameron, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 17/161,966

(22) Filed: Jan. 29, 2021

(51) Int. Cl.
A61B 17/66 (2006.01)
A61B 17/64 (2006.01)

(52) U.S. Cl.
CPC ...... A61B 17/6408 (2013.01); A61B 17/6425 (2013.01); A61B 17/66 (2013.01)

(58) Field of Classification Search
CPC .. A61B 17/6408; A61B 17/6425; A61B 17/66
USPC ............................................ 606/57; 128/882
See application file for complete search history.

(56) References Cited

U.S. PATENT DOCUMENTS

| 2,057,992 | A | 10/1936 | Wiruth |
| 4,782,827 | A | 11/1988 | Paratte |
| 5,025,802 | A | 6/1991 | Laico et al. |
| 5,063,918 | A | 11/1991 | Guhl |
| 5,582,379 | A * | 12/1996 | Keselman ............. A61F 5/3761 248/229.25 |
| 6,234,173 | B1 * | 5/2001 | Hajianpour ............ A61G 13/12 128/869 |
| 6,826,794 | B2 | 12/2004 | Mahoney et al. |
| 7,947,862 | B2 | 5/2011 | Livorsi |
| 8,048,082 | B1 | 11/2011 | DeMayo |
| 9,056,042 | B2 | 6/2015 | Russell |
| 9,314,272 | B1 | 4/2016 | Demayo |
| 9,545,351 | B2 | 1/2017 | Sommer et al. |
| 9,615,987 | B2 | 4/2017 | Worm et al. |
| 9,693,923 | B2 | 7/2017 | Aboujaoude et al. |
| 9,951,904 | B2 | 4/2018 | Perez et al. |
| 10,105,274 | B2 | 10/2018 | Carn |
| 10,265,235 | B2 | 4/2019 | Limoni et al. |
| 10,292,887 | B2 | 5/2019 | King |
| 10,357,236 | B2 | 7/2019 | DeMayo et al. |
| 10,357,237 | B2 | 7/2019 | DeMayo et al. |
| 10,478,364 | B2 | 11/2019 | Fossez et al. |
| 10,485,721 | B2 | 11/2019 | Ferro et al. |
| 10,617,404 | B2 | 4/2020 | DeMayo et al. |
| 10,660,816 | B2 | 5/2020 | Limoni et al. |
| 2010/0192961 | A1 * | 8/2010 | Amiot ..................... A61G 13/12 128/882 |
| 2013/0019883 | A1 * | 1/2013 | Worm .................. A61G 13/125 128/882 |

(Continued)

Primary Examiner — Eduardo C Robert
Assistant Examiner — David C Comstock

(57) ABSTRACT

Systems and methods include stabilizing a leg and providing femoral distraction during a knee arthroplasty surgery. The disclosed systems include a leg holder to receive a foot of a patient and a femoral distractor received in the leg holder and disposed underneath a knee of the patient. The femoral distractor is actuated to increase or decrease in length to distract the femur such that a surgeon may cut to resection the femur without also simultaneously providing distraction of the femur.

20 Claims, 9 Drawing Sheets

(56) References Cited

U.S. PATENT DOCUMENTS

2014/0101851 A1\* 4/2014 Schuerch, Jr. ..... A61G 13/1245
 5/624
2017/0049654 A1 2/2017 DeMayo et al.
2019/0336172 A1\* 11/2019 Wurapa .............. A61B 17/6416
2020/0261297 A1 8/2020 Strydom et al.

\* cited by examiner

SYSTEMS AND METHODS FOR LEG STABILIZATION DURING KNEE ARTHROPLASTY SURGERY

FIELD

The present disclosure generally relates to knee arthroplasty and, in particular, to systems and methods for stabilizing the leg and providing femoral distraction during a knee arthroplasty procedure.

BACKGROUND

Knee arthroplasty, often called a knee replacement, is a surgical procedure used to reconstruct and resurface a knee that has been damaged, such as by arthritis. Total knee arthroplasty devices replace both the tibiofemoral joint and the patellafemoral joint. The tibiofemoral joint is where the tibia and the femur articulate. The patellafemoral joint is where the patella and the femur articulate. To replace the tibiofemoral joint, knee arthroplasty includes a femoral trial (or implant) secured to the distal end of the femur, a tibial tray (or implant) secured to the proximal end of the tibia, and an insert disposed therebetween. The femoral implant and tibial implant cap the ends of the femur and tibia, respectively, which form the knee joint, thereby reconstructing the knee. To replace the patellafemoral joint, knee arthroplasty includes a patella prostheses (or implant) to replace the backside of the patella and form a replacement articulating surface which interfaces with the femoral trial. Knee arthroplasty surgery can also be achieved through the use of a robot providing trajectory and navigation information to the surgeon performing the procedure.

To achieve accurate resections in robotic total knee arthroplasty, relative motion between the bony anatomy being resected and the cutting instrument performing the resection must be minimized. One option to minimize this motion is to stabilize the leg via auxiliary leg fixation. Auxiliary leg stabilization can be achieved via coupling the leg to the table or via coupling the leg to the floor.

In existing systems and methods for auxiliary leg stabilization, a patient's foot and ankle are supported in a boot, which is attached to a bed mounted rail. By manipulating a boot locking mechanism to the rail, the surgeon is able to place the leg in extension and flexion and internally and externally rotate the knee joint. Existing systems and methods have several disadvantages. They do not provide any direct support of the femur during the resection, do not distract the femur, and do not provide any considerations for retractor holding during the procedure.

What is needed are auxiliary leg stabilization systems and method that overcome the existing disadvantages noted above.

SUMMARY

According to one embodiment, a leg stabilization device for fixating a leg during knee arthroplasty surgery. The device includes a leg holder that has a rail, a boot carriage coupled to the rail, and a boot configured to be secured the rail by being received by the boot carriage. The leg stabilization device also includes a femoral distractor carriage received in the rail and a femoral distractor secured to the leg holder. The femoral distractor includes a ball end, an actuator, and a block end, wherein the ball end is received in the femoral distractor carriage. According to another embodiment, a method for stabilization a leg of a patient for knee arthroplasty surgery. The method includes providing a leg holder that has a rail, a boot carriage coupled to the rail, and a boot configured to be secured the rail by being received by the boot carriage. The method further includes providing a femoral distractor carriage to be received in the rail. Providing a femoral distractor to be secured to the leg holder. The femoral distractor includes a ball end, an actuator, and a block end, wherein the ball end is received in the femoral distractor carriage. The method further includes securing the rail to a bed or table, installing the boot carriage to the rail, securing the boot to the boot carriage, securing a foot of the patient to the boot, installing the femoral distractor carriage to the rail, securing the femoral distractor in the femoral distractor carriage, and actuating the femoral distractor for a femoral resection.

BRIEF DESCRIPTION OF THE DRAWINGS

Corresponding reference characters indicate corresponding parts throughout the drawings.

DETAILED DESCRIPTION OF THE DISCLOSURE

Various different systems and methods for providing auxiliary leg stabilization to carry out and perform knee arthroplasty are disclosed here.

Figure 1:
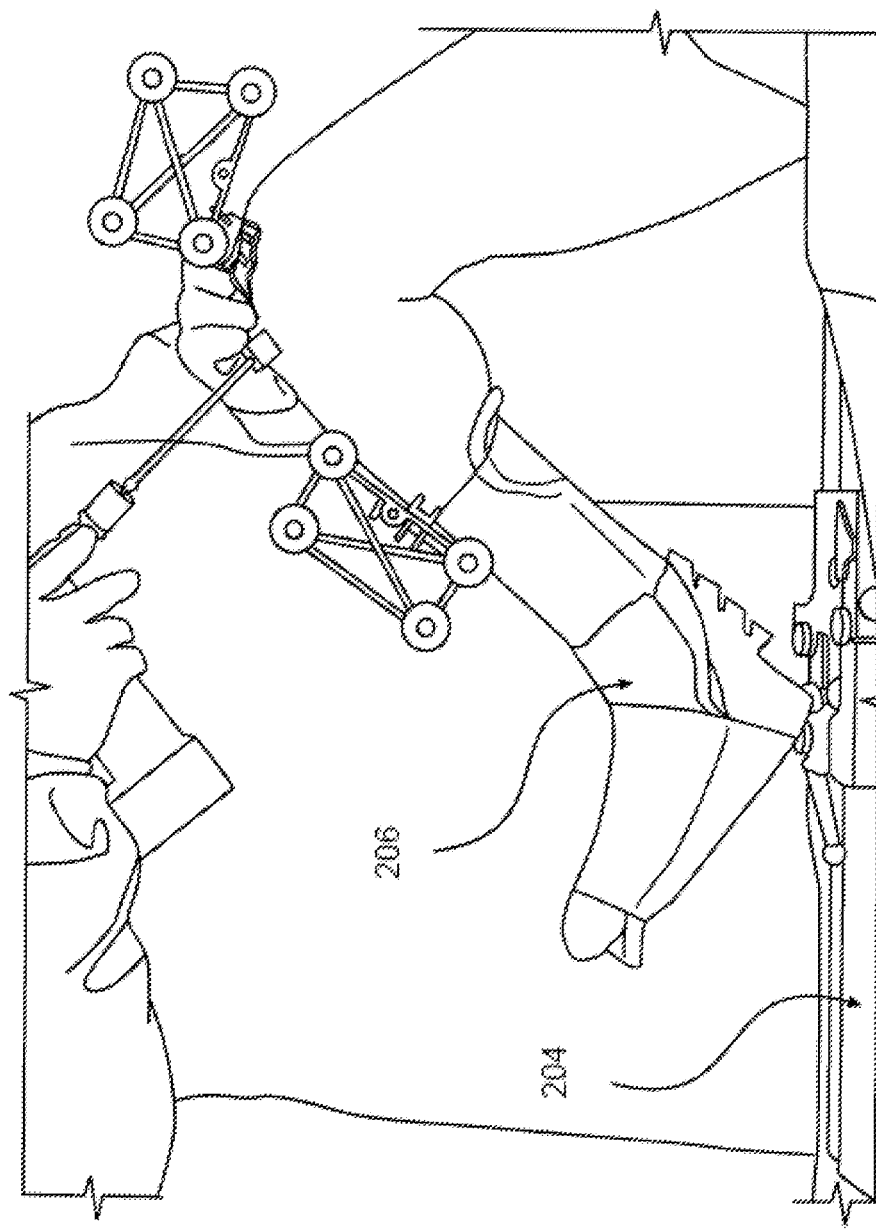
FIG. 1 illustrates a conventional leg holder.

FIG. 1 illustrates a conventional leg holder which includes a bed mounted rail that attaches to a boot. A patient's foot rests in the boot as the surgery is conducted. While in this case, the tibia is stabilized, the femur is not and may move during the surgery. This may be problematic during resection and distraction of the femur. FIG. 1 also shows navigation arrays attached to femur and tibia to facilitate navigation of the tool during robot assisted surgery.

Figure 2:
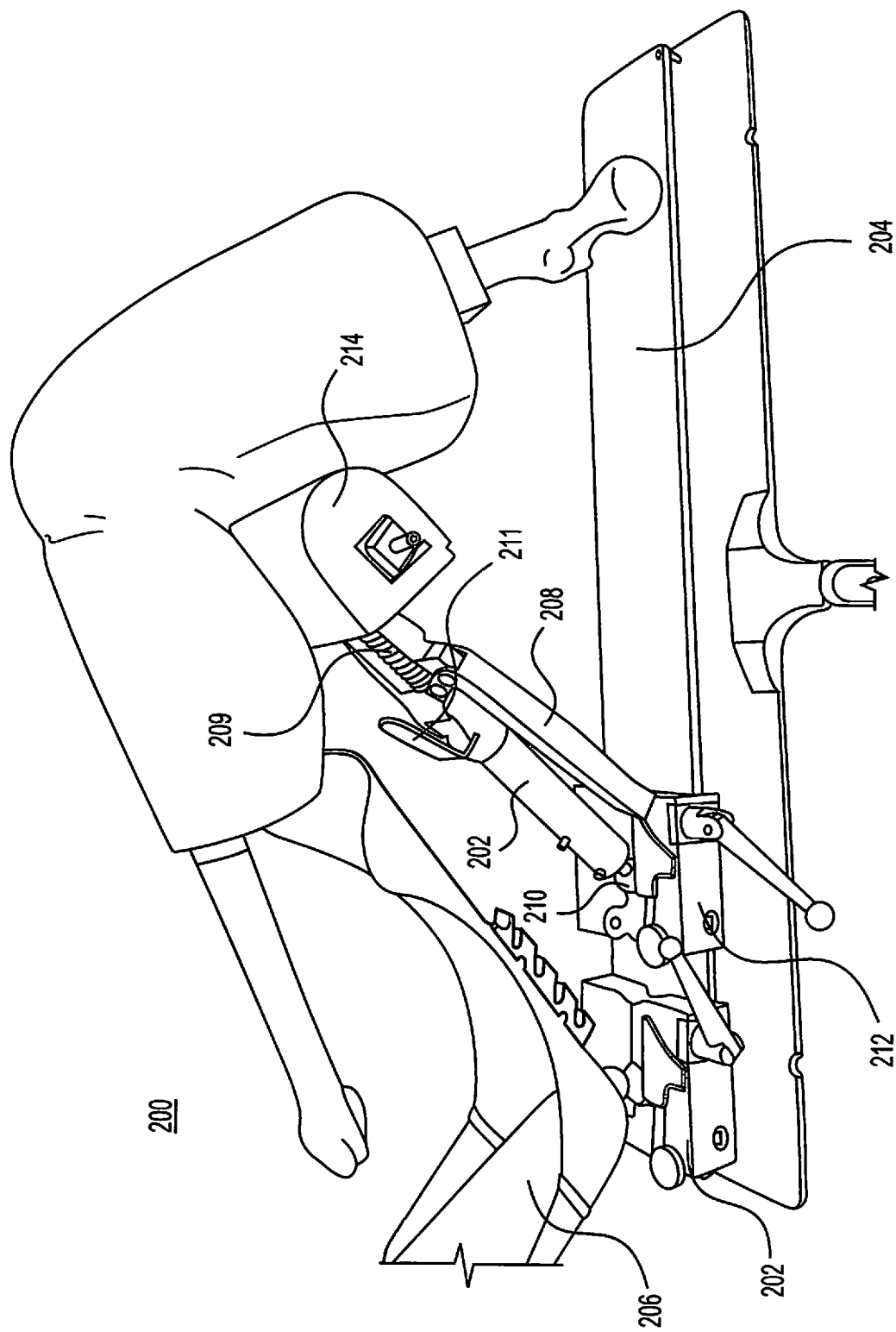
FIG. 2 illustrates an exemplary embodiment of an auxiliary leg stabilization device consistent with the principles of the present disclosure.

Consistent with the principles of the current disclosure, and as illustrated in FIG. 2, a leg holder 200 may include a femoral distractor 202 that attaches to a bed mounted rail 204 that also supports a boot 206. Femoral distractor 202 may be actuated via a hand pumped ratchet 208 and other actuations methods are also feasible. Femoral distractor may contain a spring 209 that is manipulated by actuator 208 to extend the length of femoral distractor 202. Femoral distractor may also have a release mechanism 211 to release tension of spring 209 and return femoral distractor 202 to a default length. A ball end 210 of femoral distractor 202 is placed in a carriage 212 that is secured to rail 204. A pillow block end 214 is placed under the posterior femur. In operation, the patient's foot is placed in boot 206 and femoral distractor 202 is actuated by ratchet 208 to distract the femur. The surgeon may then resection the femur according to the surgical plan.

Figure 8:
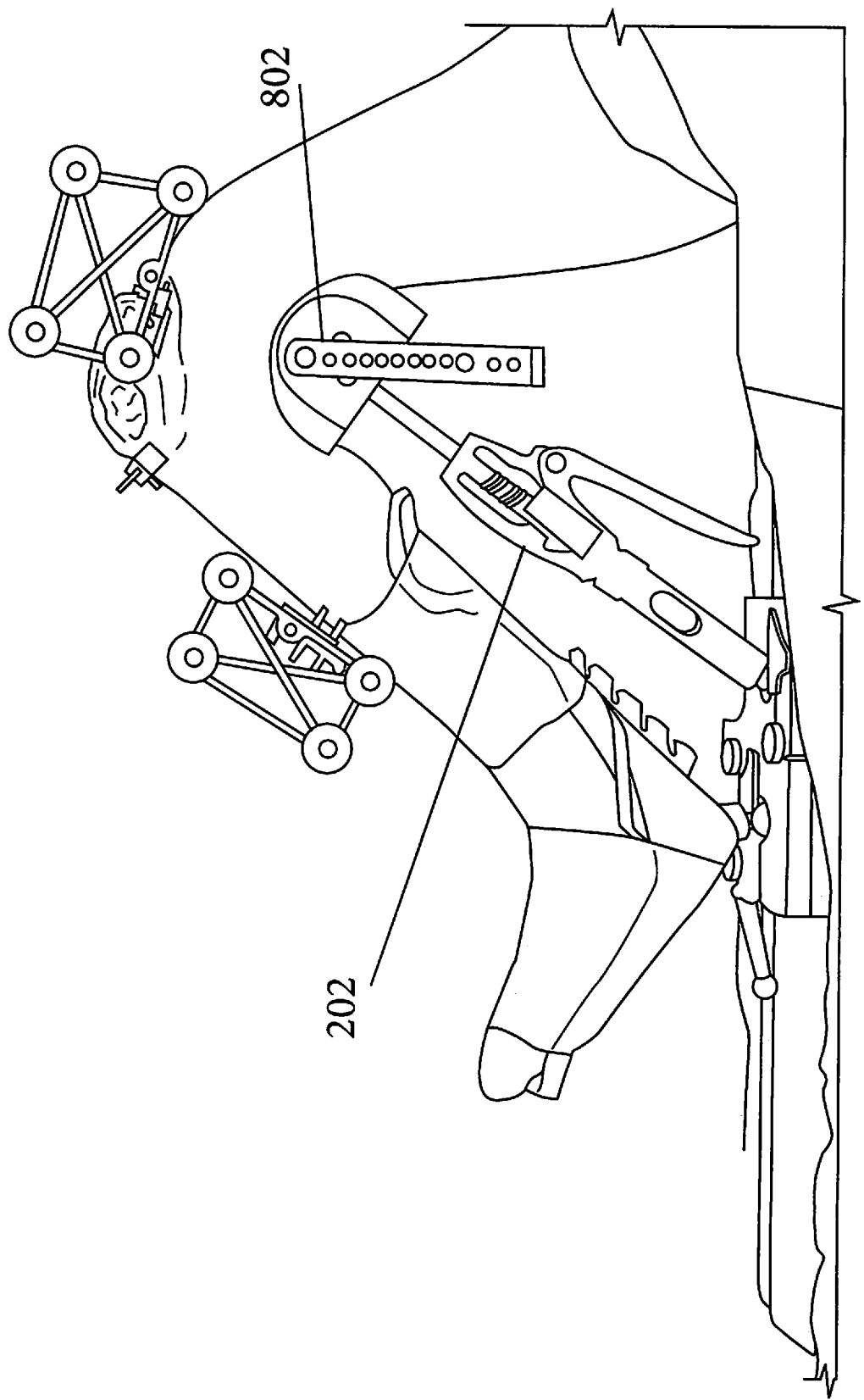
FIG. 8 illustrates an exemplary embodiment of an auxiliary leg stabilization device consistent with the principles of the present disclosure.
Figure 9:
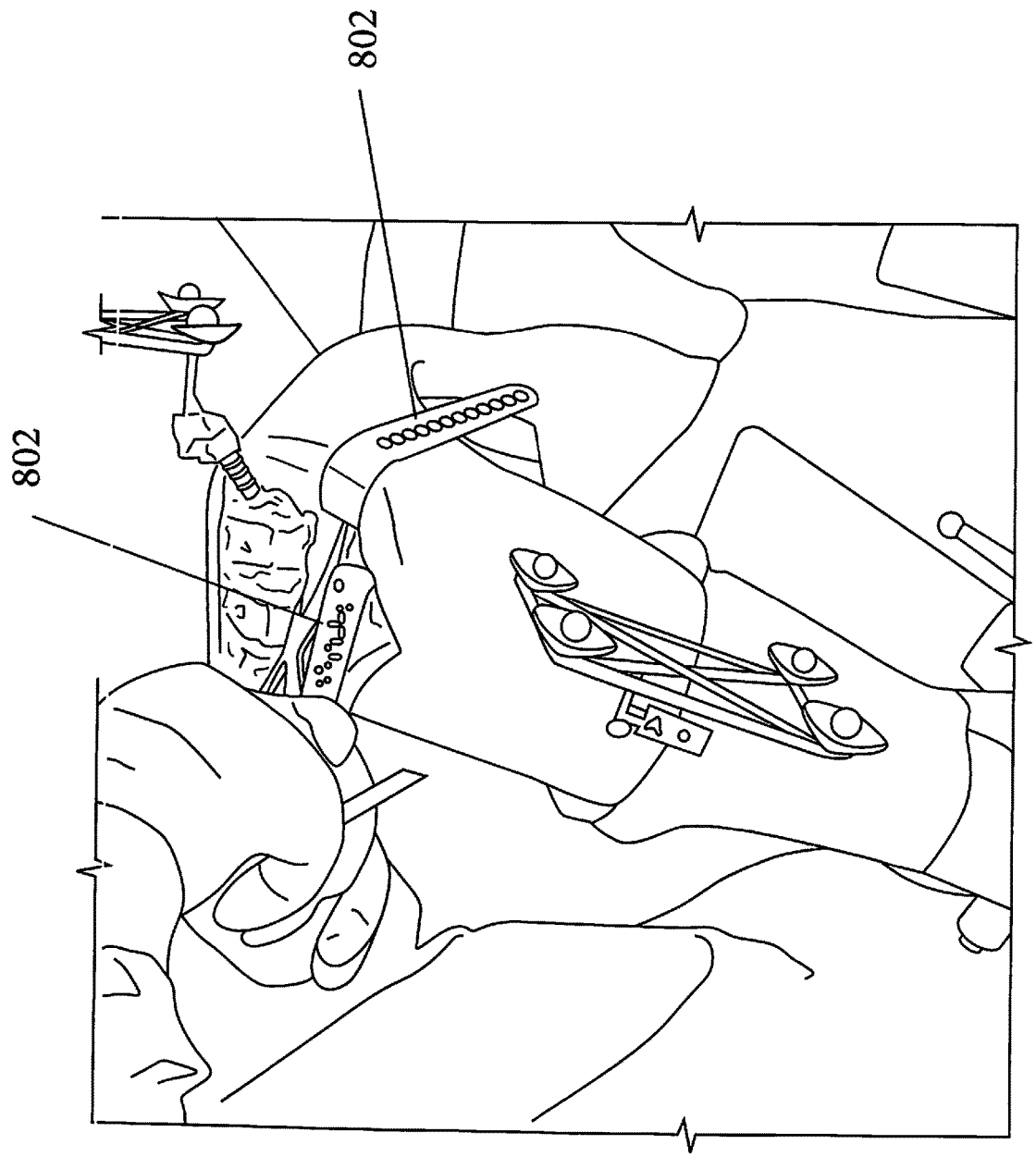
FIG. 9 illustrates an exemplary embodiment of an auxiliary leg stabilization device consistent with the principles of the present disclosure.

The femoral distractor of the present disclosure achieves objectives that are not supported by a conventional leg holder. This includes but is not limited to supporting the femur during resection, providing for the ability to distract the femur, and providing an attachment point for retractors to facilitate hands free retraction. As shown in FIGS. 8 and 9, femoral distractor 202 may serve as an attachment point for retractors 802. This allows hands free retraction to perform the femoral resection.

Figure 3:
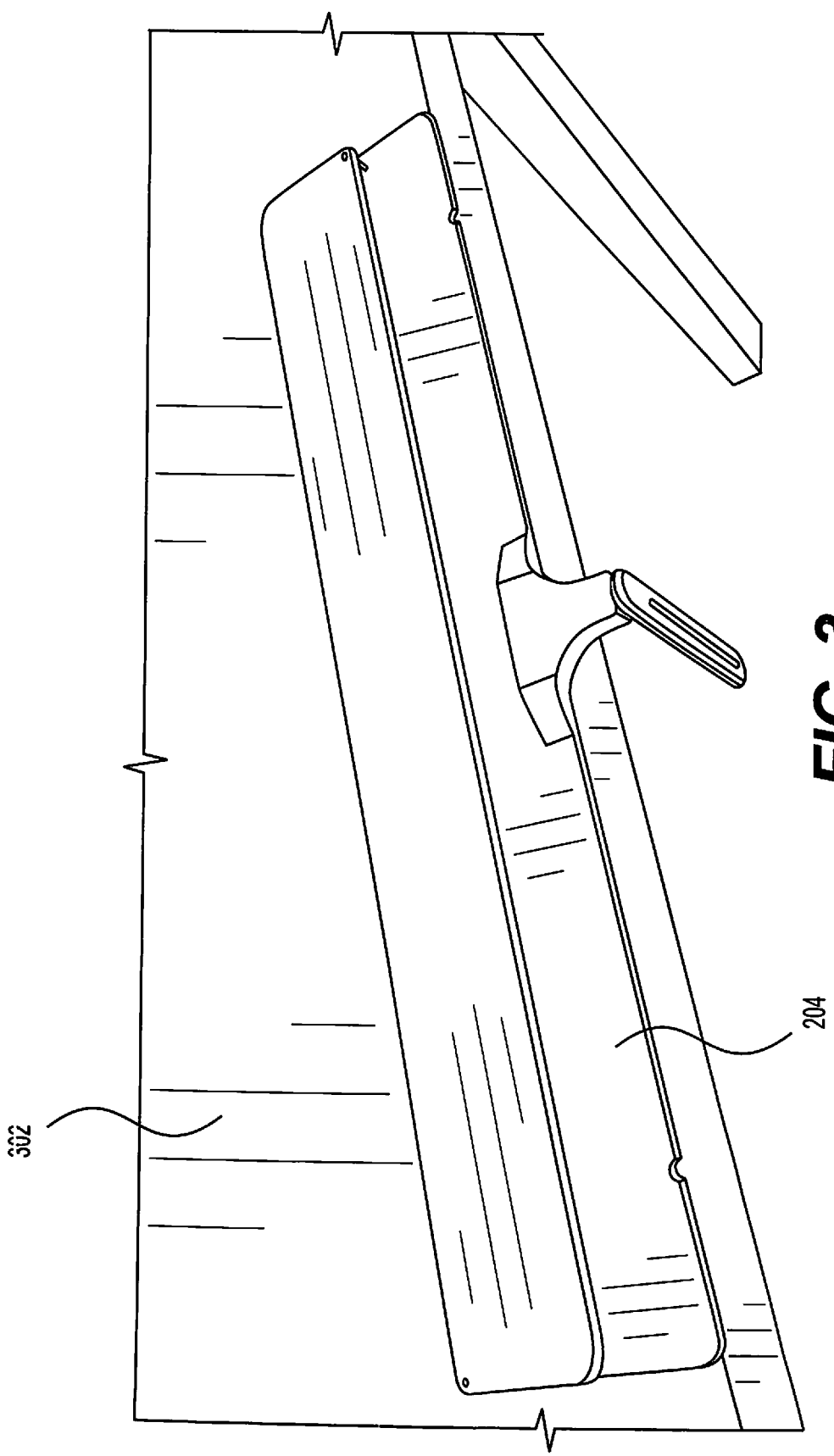
FIG. 3 illustrates a rail of an exemplary embodiment of an auxiliary leg stabilization device consistent with the principles of the present disclosure.
Figure 4:
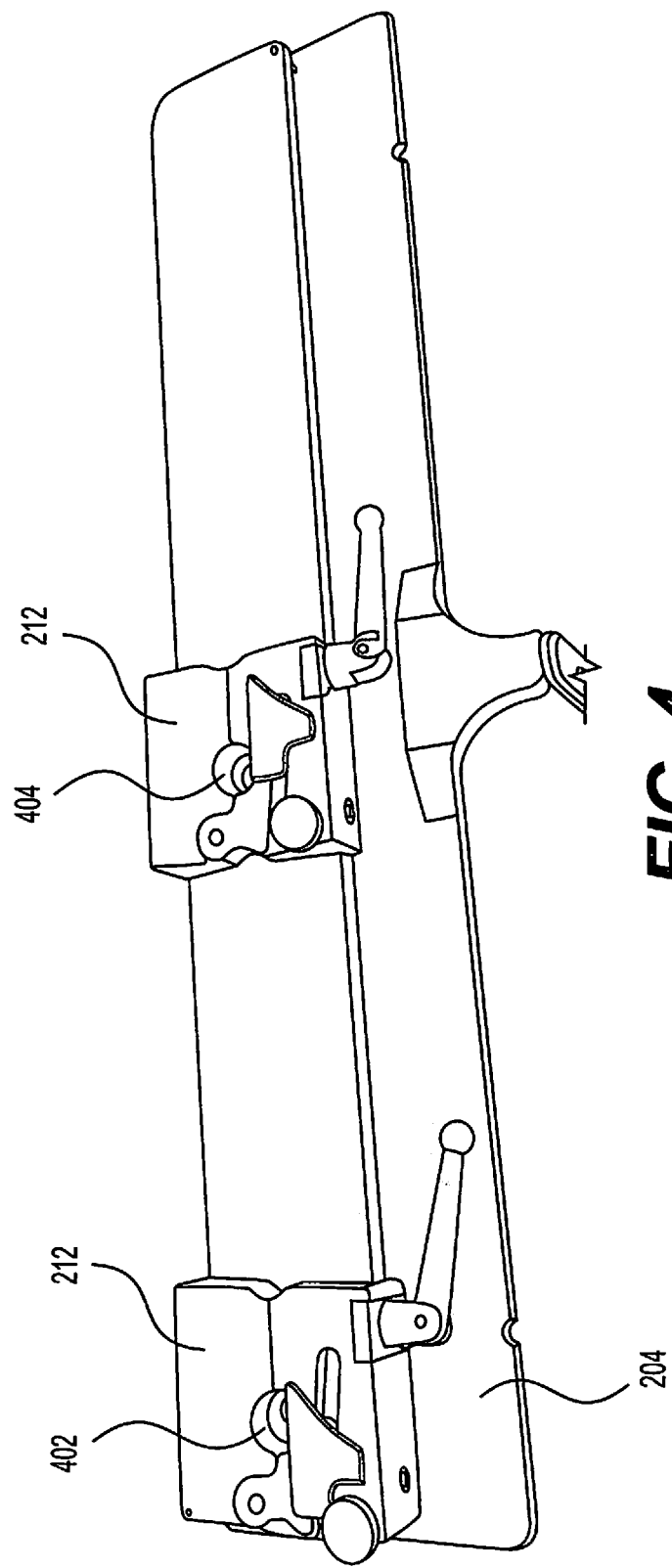
FIG. 4 illustrates a rail and carriages of an exemplary embodiment of an auxiliary leg stabilization device consistent with the principles of the present disclosure.
Figure 5:
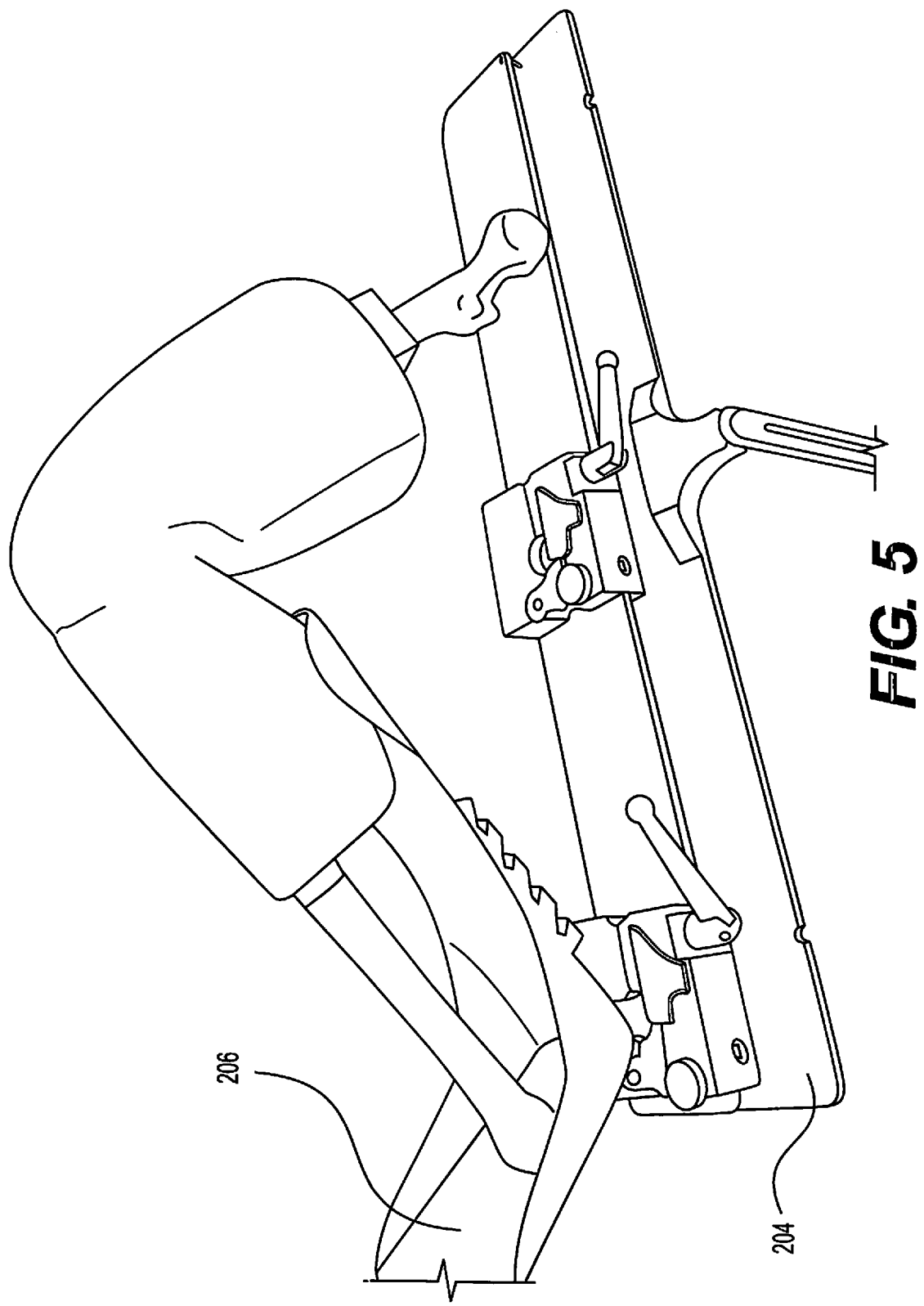
FIG. 5 illustrates a foot being secured to portions of an exemplary embodiment of an auxiliary leg stabilization device consistent with the principles of the present disclosure.

In an exemplary embodiment, the resection process and exemplary auxiliary leg stabilization device may be described as follows. Rail 204 may be placed on a bed or table 302 as shown in FIG. 3. Carriages 212 may be installed on rail 204 as shown in FIG. 4. Carriages may include a receiving hole 402 configured to receive boot 206 and a receiving hole 404 configured to receive ball end 210 of femoral distractor 202. A patient's foot may be placed in boot 206 and secured to rail 204 as shown in FIG. 5. At this point the surgeon makes an incision in the knee to facilitate the knee arthroplasty surgery. Femoral distractor 202 is placed in bed rail 204 and the femur is distracted as previously shown in FIG. 2. Retractors are placed and coupled to femoral distractor 202 so that the femoral resection can be performed by the surgeon.

Figure 6:
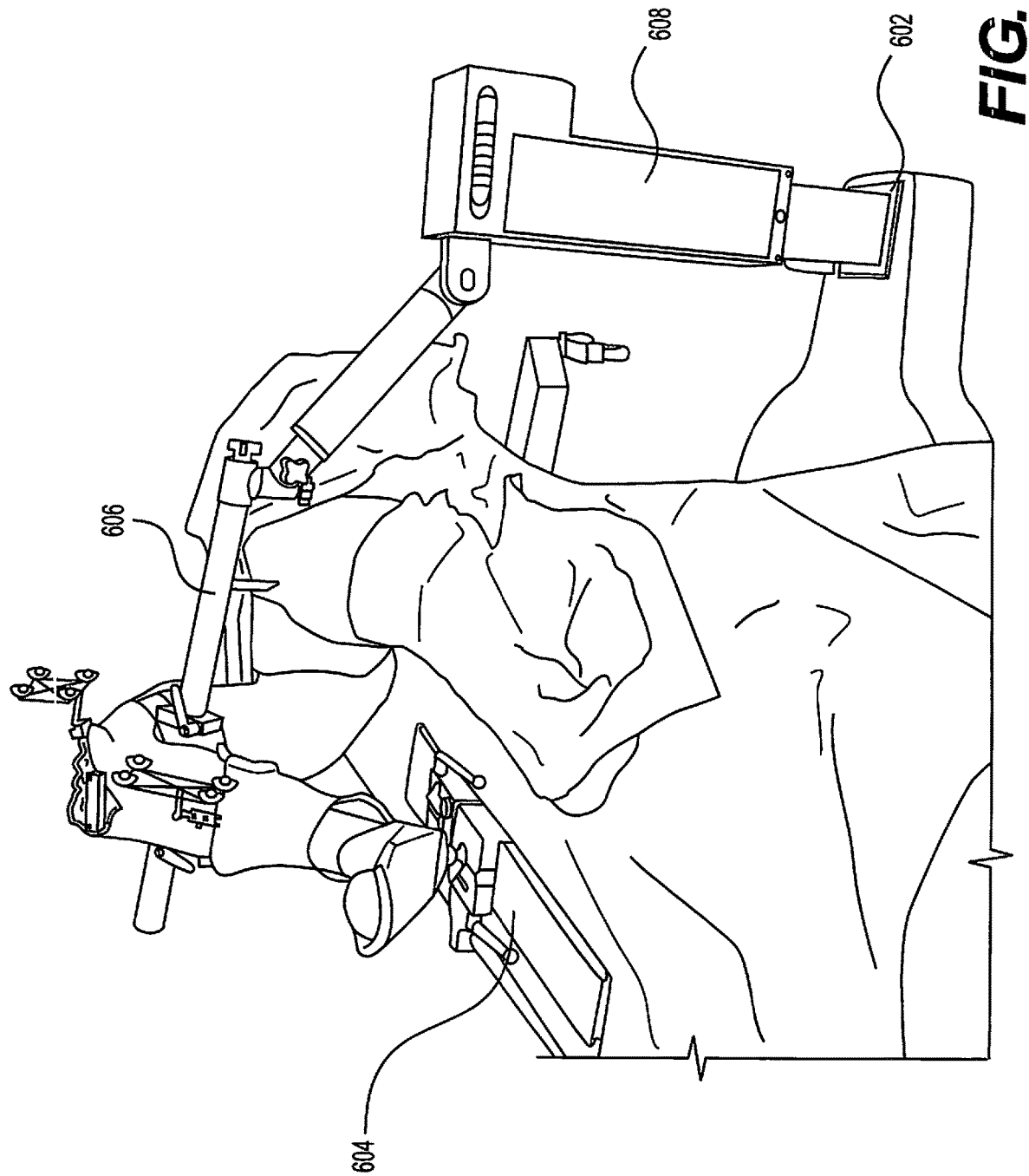
FIG. 6 illustrates an exemplary embodiment of an auxiliary leg stabilization device consistent with the principles of the present disclosure.
Figure 7:
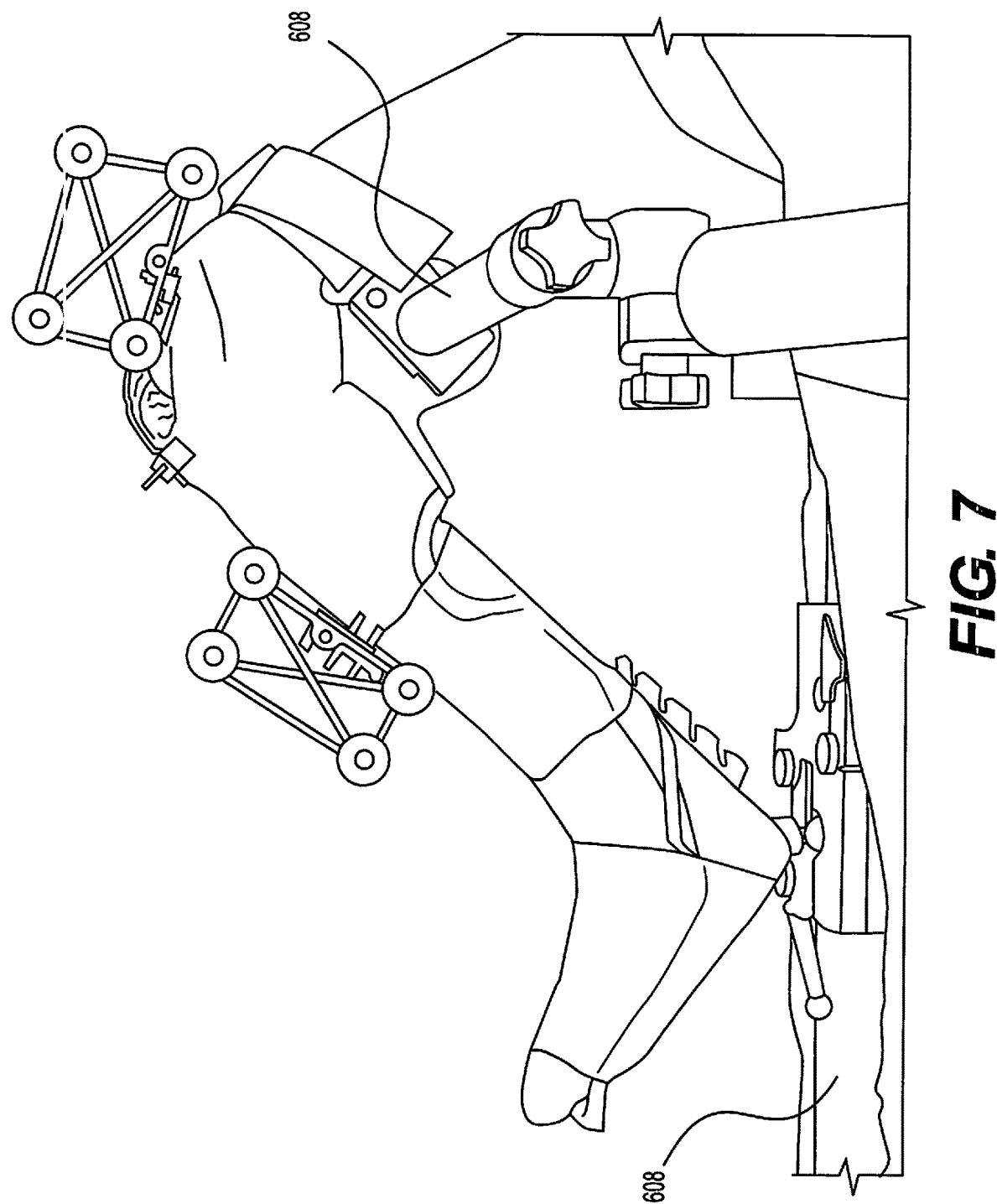
FIG. 7 illustrates an exemplary embodiment of an auxiliary leg stabilization device consistent with the principles of the present disclosure.

As an alternative system and method of leg stabilization, the leg may be coupled to a floor mounted stand 602 as shown in FIG. 6. Here, the leg may be fixated as follows. Stand 602 is positioned contralaterally to the leg. The leg is placed in flexion and the tibia secured in a bed mounted leg holder 604. A stand arm 606 is placed on the posterior femur and the femur is secured to the stand as shown in FIG. 7. At this point, a stand column 608 can be raised to provide femoral distraction for the resection process as noted above.

As various changes could be made in the above constructions, products, and methods without departing from the scope of the disclosure, it is intended that all matter contained in the above description and shown in the accompanying drawings shall be interpreted as illustrative and not in a limiting sense.

What is claimed is:

1. A leg stabilization device for fixating a leg during knee arthroplasty surgery, the device comprising:
   a rail;
   a leg holder including:
      a boot carriage configured to be slidably coupled to the rail; and
      a boot configured to be secured to the rail by being received by the boot carriage,
   a femoral distractor carriage configured to be slidably coupled to the rail and to be slidable independent of the boot carriage; and
   a femoral distractor configured to be secured to the femoral distractor carriage, the femoral distractor including a ball end adapted to be received in the femoral distractor carriage, an actuator, and a block end, the femoral distractor further having a support block adapted to be attached to the block end and at least one retractor attachable to the block end and adapted to retract tissue around the knee.

2. The leg stabilization device of claim 1, wherein the boot is configured to receive a foot of a patient and the femoral distractor is configured to be disposed underneath a knee of the patient.

3. The leg stabilization device of claim 2, wherein the ball end and the femoral distractor carriage are secured as a ball and socket joint.

4. The leg stabilization device of claim 3, wherein the block end is configured to rest underneath the knee of the patient.

5. The leg stabilization device of claim 2, wherein the actuator is configured to extend a length of the femoral distractor to distract a femur of the patient for resection.

6. The leg stabilization device of claim 5, wherein the actuator is a hand pumped ratchet.

7. The leg stabilization device of claim 6, wherein the femoral distractor includes a spring and a release mechanism.

8. The leg stabilization device of claim 7, wherein the actuator is configured to provide tension on the spring causing the femoral distractor to increase in length.

9. The leg stabilization device of claim 8, wherein the release mechanism is configured to release tension in the spring to cause the femoral distractor to decrease in length.

10. The leg stabilization device of claim 1, wherein the at least one retractor includes a pair of retractors configured to be secured to ends of the support block.

11. A method for stabilization of a leg of a patient for knee arthroplasty surgery, the method comprising:
    providing a leg holder, the leg holder including:
       a boot carriage configured to be slidably coupled to a rail; and
       a boot configured to be secured to the rail by being received by the boot carriage,
    providing a femoral distractor carriage configured to be slidably coupled to the rail and to be slidable independent of the boot carriage;
    providing a femoral distractor configured to be secured to the femoral distractor carriage, the femoral distractor including a ball end adapted to be received in the femoral distractor carriage, an actuator, and a block end, the femoral distractor further having a support block adapted to be attached to the block end and at least one retractor attachable to the block end and adapted to retract tissue around the knee;
    securing the rail to a bed or table;
    installing the boot carriage to the rail;
    securing the boot to the boot carriage;
    securing a foot of the patient to the boot;
    installing the femoral distractor carriage to the rail;
    securing the femoral distractor in the femoral distractor carriage;
    attaching the at least one retractor to the block end and retracting tissue around the knee; and
    actuating the femoral distractor for a femoral resection.

12. The method of claim 11, wherein the boot is configured to receive a foot of a patient and the femoral distractor is configured to be disposed underneath a knee of the patient.

13. The method of claim 12, wherein the ball end and the femoral distractor carriage are secured as a ball and socket joint.

14. The method of claim 13, wherein the block end is configured to rest underneath the knee of the patient.

15. The method of claim 12, wherein the actuator is configured to extend a length of the femoral distractor to distract a femur of the patient for resection.

16. The method of claim 15, wherein the actuator is a hand pumped ratchet configured to extend the femoral distractor.

17. The method of claim 16, wherein the femoral distractor includes a spring and a release mechanism.

18. The method of claim 17, wherein the actuator is configured to provide tension on the spring causing the femoral distractor to increase in length.

19. The method of claim 18, wherein the release mechanism is configured to release tension in the spring to cause the femoral distractor to decrease in length.

20. The method of claim 11, wherein the at least one retractor includes a pair of retractors, the method comprising attaching the pair of retractors to ends of the support block.

* * * * *